US011426604B2

(12) United States Patent
Tillander

(10) Patent No.: US 11,426,604 B2
(45) Date of Patent: Aug. 30, 2022

(54) MOCK-UP ANTENNA AND COIL SYSTEM

(71) Applicant: KONINKLIJKE PHILIPS N.V., Eindhoven (NL)

(72) Inventor: Matti Oskari Tillander, Vantaa (FI)

(73) Assignee: Koninklijke Philips N.V., Eindhoven (NL)

( * ) Notice: Subject to any disclaimer, the term of this patent is extended or adjusted under 35 U.S.C. 154(b) by 750 days.

(21) Appl. No.: 16/322,671

(22) PCT Filed: Aug. 7, 2017

(86) PCT No.: PCT/EP2017/069882
§ 371 (c)(1),
(2) Date: Feb. 1, 2019

(87) PCT Pub. No.: WO2018/029122
PCT Pub. Date: Feb. 15, 2018

(65) Prior Publication Data
US 2021/0353962 A1 Nov. 18, 2021

(30) Foreign Application Priority Data
Aug. 8, 2016 (EP) ..................... 16183154

(51) Int. Cl.
*A61N 5/10* (2006.01)
*A61B 5/055* (2006.01)
(Continued)

(52) U.S. Cl.
CPC .......... *A61N 5/1039* (2013.01); *A61B 5/055* (2013.01); *A61N 5/1037* (2013.01);
(Continued)

(58) Field of Classification Search
CPC ............... A61N 5/1039; A61N 5/1037; A61N 5/1049; A61N 2005/1055;
(Continued)

(56) References Cited

U.S. PATENT DOCUMENTS

| 6,138,302 A * | 10/2000 | Sashin ................ A61B 6/0487 5/600 |
| 8,905,035 B2 | 12/2014 | Wilson |
| 9,081,067 B2 | 7/2015 | Schellekens |
| 9,204,818 B2 | 12/2015 | Moffatt |

(Continued)

FOREIGN PATENT DOCUMENTS

| JP | 360642 | 3/1991 |
| JP | 2004097431 A | 4/2004 |
| WO | 2004024235 A1 | 3/2004 |

*Primary Examiner* — Sean D Mattson

(57) ABSTRACT

It is an object of the invention to address the above mentioned issues related to image quality and patient positioning. This object is achieved by a mock-up antenna configured to be used during radiation treatment delivery, wherein the radiation treatment is delivered based on a radiation treatment plan and wherein the radiation treatment plan is at least partly based on a planning magnetic resonance image. The mock-up antenna is substantially transparent to radiation and comprises connection means configured to allow a connection between the mock up antenna and a fixation means, which fixation means is configured to fixate a position of the mock-up antenna during radiation treatment and. The mock-up antenna further comprises an inner surface configured to be positioned towards a patient in a way such that is affects a position and/or orientation of the patient during radiation treatment delivery, wherein the inner surface has a shape substantially similar to a shape of a working magnetic resonance imaging antenna used during an acquisition of the planning magnetic resonance image.

17 Claims, 1 Drawing Sheet

(51) Int. Cl.
*G01R 33/341* (2006.01)
*G01R 33/48* (2006.01)

(52) U.S. Cl.
CPC ......... *A61N 5/1049* (2013.01); *G01R 33/341* (2013.01); *G01R 33/4808* (2013.01); *A61N 2005/1055* (2013.01); *A61N 2005/1063* (2013.01)

(58) Field of Classification Search
CPC ............ A61N 2005/1063; A61B 5/055; G01R 33/341; G01R 3/4808
See application file for complete search history.

(56) References Cited

U.S. PATENT DOCUMENTS

| | | |
|---|---|---|
| 9,468,777 B2 | 10/2016 | Fallone |
| 9,739,853 B2 | 8/2017 | Everett |
| 10,918,887 B2 | 2/2021 | Shvartsman |
| 2005/0165291 A1* | 7/2005 | Hadley ................. A61B 5/055 600/407 |
| 2007/0270683 A1* | 11/2007 | Meloy ................. A61G 13/121 600/415 |
| 2010/0329414 A1* | 12/2010 | Zhu ..................... A61B 6/4417 378/4 |
| 2011/0050226 A1 | 3/2011 | Schellekens et al. |
| 2013/0027040 A1 | 1/2013 | Alagappan et al. |
| 2013/0190604 A1* | 7/2013 | Moffatt ................. A61B 5/055 600/411 |
| 2013/0218000 A1 | 8/2013 | Coppens |
| 2014/0121497 A1 | 5/2014 | Coppens et al. |
| 2015/0112187 A1* | 4/2015 | Petropoulos ......... A61B 6/0421 600/422 |

* cited by examiner

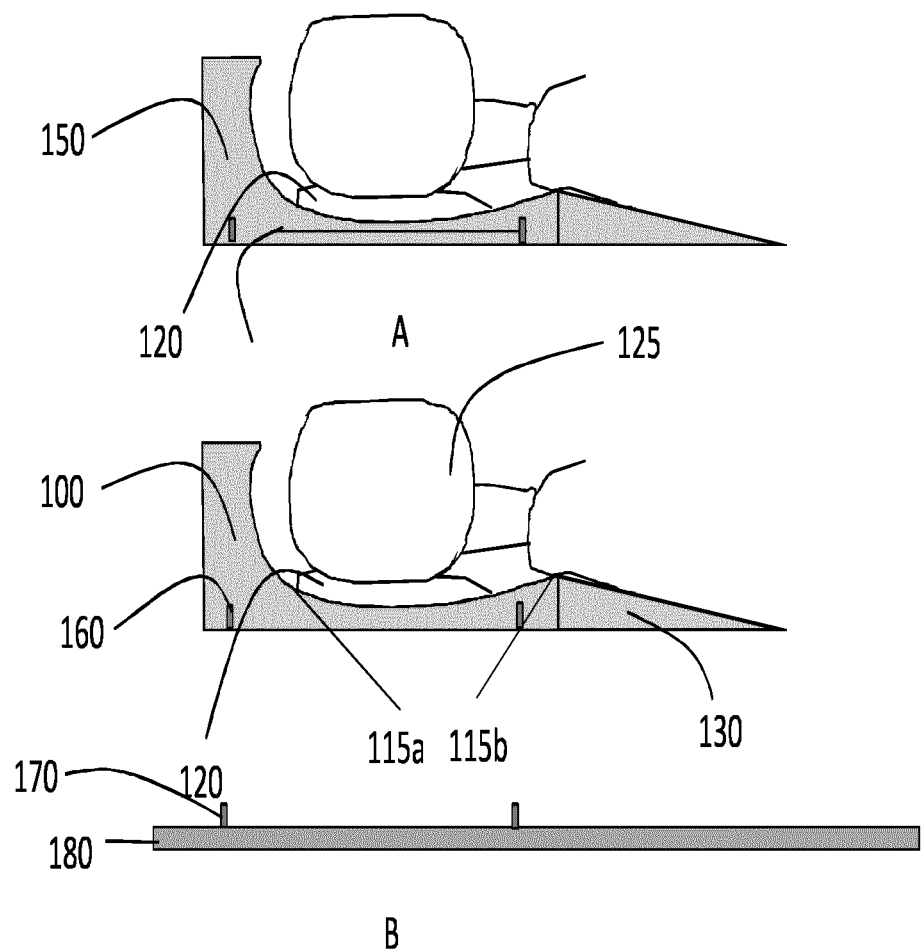

MOCK-UP ANTENNA AND COIL SYSTEM

CROSS REFERENCE TO RELATED APPLICATIONS

This application is a U.S. national phase application of International Application No. PCT/EP2017/069882, filed on Aug. 7, 2017, which claims the benefit of EP Application Serial No. 16183154.0 filed on Aug. 8, 2016 and is incorporated herein by reference.

FIELD OF THE INVENTION

The invention relates to field of radiation treatment and more specifically to the use of magnetic resonance imaging for radiation treatment.

BACKGROUND OF THE INVENTION

Computed tomography (CT) images and magnetic resonance imaging (MRI) images are nowadays routinely utilized in the radiation therapy (RT) planning. In order to ensure safe and effective treatment, it is important that the same patient position and orientation is used in the treatment at linear accelerator (linac) table as was used during the imaging session prior to treatment planning. To improve patient positioning, for example, a flat tabletop can be used at MRI when imaging for RT purposes instead of the regular curved MRI imaging tabletop since also the linac treatment table is flat.

MRI uses specialized detecting coils to record the MRI signals. Due to coil geometry it may not be always possible to setup the patient so that it would be similar to what is used at the linac, or alternative coil solutions need to be used. For example, diagnostic brain imaging is done using a head coil, but for radiation therapy planning purposes another coil solution needs to be used to enable using the flat tabletop and head mask needed for head fixation. Not being able to use the head coil may mean a compromise in the image quality, especially respect to geometrical accuracy and image intensity homogeneity. This may be a major disadvantage in possible MRI-only brain applications where the therapy planning for brain radiation treatment would be done solely based on MRI images.

The use of MRI coils in combination with irradiation is for example described in US 2011/0050226A1. US 2011/0050226A1 describes an RF coil used for MR imaging that is designed so that it remains in place in the field of view of an X-Ray imaging system and comprises a support board on which copper conductive traces and copper printed capacitors are carried. The attenuation of the X-Rays caused by the copper traces is visible in the radiation image but this is compensated by arranging the non-conductive material of the support board such that the attenuation of substantially the whole of the RF coil located within the field of view is substantially constant throughout the field of view.

SUMMARY OF THE INVENTION

It is an object of the invention to address the above mentioned issues related to image quality and patient positioning. This object is achieved by a mock-up antenna according to claim 1. The object is also achieved by a coil system according to claim 4.

By means of the invention, normal diagnostic radiofrequency (RF) coils can be used during imaging prior to radiation treatment for the purpose to be used for radiation treatment planning. The terms radiation treatment or radiation treatment delivery in this context designate the application of a first kind of radiation (or first radiation, or therapeutic radiation) to a (part or parts of) a patient's body for therapeutic purposes, e.g. the radiation produced by a linear accelerator or any other kind of radiation producing device, that is or may be used for therapeutic purposes in nuclear medicine. In some embodiments of the invention, the first kind of radiation may also be a radio frequency radiation.

The possibility of using standard diagnostic RF coils may improve the image quality of the resulting MRI images. It is considered very important in the field of radiation treatment that the position of the patient while being on the treatment table accurately matches the position he had when the planning images were acquired. This requirement is addressed by the invention by means of the mock-up coil having an inner surface configured to be positioned towards a patient during radiation treatment delivery in a way such that it affects the patient's position and/or orientation. In other words, the inner surface has a shape substantially similar to a shape of a working magnetic resonance antenna used during the acquisition of the planning MRI. Because both the working antenna and the mock up antenna have a similar outline for the inner surface both antennas will deform and/or orient the patient in a similar way and thereby patient positioning can be done sufficiently reproducible. The mock-up (and corresponding working antenna) may be positioned in direct contact with the patient. However, there may also be non-direct contact between the patient and the (mock-up) antenna for example thermoweldable material, like e.g. a pillow may be positioned between the patient and the (mock-up) antenna. In order to accurately (re)position the patient it is desirable to fixate the (mock-up) antenna in a certain position. Therefore, the (mock-up) antenna comprises connection means configured to allow a connection between the mock up antenna and a fixation means. The fixation means is in turn configured to fixate a position of the mock-up antenna during radiotherapy. The connection means could be any location on the (mock-up) antenna suitable for connecting a fixation means to. A fixation means is not necessarily a part of the (mock-up) antenna, but could also be part of for example the MRI system and/or patient support. The fixation means could for example be a pillow, a radiation treatment mask, an indexed table with holes and/or pins to connect to the (mock-up) antenna, screws, and/or straps. To the skilled person it will be obvious that many alternatives could be available.

According to embodiments of the invention, the fixation means are part of the (mock-up) antenna. This is advantageous, because it may limit the number of loose pieces required for setting up the patient.

According to further embodiments of the invention, the mock-up antenna may have an outline and/or appearance substantially similar to an outline and/or appearance of the (corresponding) working antenna used during the acquisition of the planning magnetic resonance image. This embodiment is advantageous, because it may make it easier for the user to see which mock-up antenna matches which working antenna. In this way positioning errors by using an incorrect mock-up antenna may be prevented. Alternatively or additionally, the mock-up antenna could be labeled such that it is easily recognizable to which working antenna it corresponds. According to other embodiments of the invention the mock-up antenna is made substantially lighter and/or smaller than the corresponding working antenna.

As described above, according to another aspect, the invention is a coil system comprising both a working antenna and a (corresponding) mock-up antenna. The mock-up antenna comprises an inner surface configured to be positioned towards the patient during radiotherapy delivery, wherein the inner surface of the mock-up antenna has a shape substantially similar to a shape of the inner surface of the working MRI antenna. Within the coil system the mock-up antenna is the same as the mock-up antenna described above. In addition to this, the coil system also comprises a working antenna. It may be advantageous for a hospital to buy a combination of a working and mock-up antenna from the same vendor, because in this way it may be easier to guarantee the similarity in shape of the inner surface. Similarly to the mock-up coil, also in the coil system the mock-up coil could comprise fixation means. The same or similar fixation means could be used in the working antenna.

These and other aspects of the invention will be apparent from and elucidated with reference to the embodiments described hereinafter.

BRIEF DESCRIPTION OF THE DRAWINGS

FIG. 1 diagrammatically shows a mock-up antenna and a working antenna according to embodiments of the invention.

DETAILED DESCRIPTION OF THE INVENTION

FIG. 1 diagrammatically shows a mock-up antenna 100 and a working antenna 150 according to embodiments of the invention. Prior to radiation treatment planning, the patient 125 is positioned in the MRI to acquire images that can be used for delineating a treatment target. In a fully MRI based workflow, MRI images may be acquired that can be used to create a radiation attenuation map. For these purposes the patient is positioned on top of a working antenna 150. In FIG. 1, only the anterior part of the antenna is shown, as in this case, this is the part of the antenna that affects patient position and orientation. In FIG. 1, a working 150 and mock-up antenna 100 are shown. It can be seen in FIG. 1 that the working antenna and the mock-up antenna have a very similar appearance. In this FIGURE, the only difference is that the working antenna 150 comprises a functioning antenna structure configured to transmit and/or receive RF signals to/from the patient. The mock-up antenna is substantially transparent to radiation, especially to the first kind of radiation, in order to limit the effect of the mock-up antenna on the dose delivered to the patient. Substantial radio transparency can be achieved by materials like carbon fibre, glass fibre, low-density plastics, and rigid or semi-rigid foams. The reproducibility of patient positioning may be further improved by positioning the patient on top of a thermoweldable pillow 120 that has been customized to this specific patient. In addition to this, a wedge 130 may be used. The MRI images acquired by means of the working antenna will serve as an input for creating a radiation treatment plan.

In most common clinical practise radiation treatment is not performed within an MRI scanner, but cone beam CT is used for positioning instead. In order to be able to reproduce the patient position and orientation of the MRI acquisition during treatment, the mock-up antenna 100 is used. The mock-up antenna comprises an inner surface configured to be positioned towards the patient 125 in a way such that is affects a position and/or orientation of the patient during radiation treatment. The inner surface has a shape substantially similar to a shape of a working magnetic resonance antenna used during an acquisition of the planning magnetic resonance image. As the inner surface is limited to the part of the mock-up antenna that is configured to affect patient position and/or shape, the inner surface in FIG. 1 is limited to the area between points 115a and 115b. In the mock-up antenna the same patient specific pillow 120 is used. The mock-up antenna further comprises connection means 160 configured to allow a connection between the mock up antenna and a fixation means 170. The fixation means are configured to fixate a position of the mock-up antenna during radiotherapy. In this embodiment the fixation means 170 are connected to the patient table in order to fixate the mock-up coil to the patient table 180.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A method for using a kit comprising a working magnetic resonance imaging antenna, wherein the working magnetic resonance imaging antenna is configured to be used for magnetic resonance imaging, and a mock-up antenna, wherein the mock-up antenna is configured to be used during radiation treatment delivery, wherein the radiation treatment is delivered based on a radiation treatment plan, wherein the radiation treatment plan is at least partly based on a planning magnetic resonance image, wherein the planning magnetic resonance image is acquired prior to the radiation treatment, where a first kind of radiation is used during the radiation treatment, wherein a second kind of radiation is used during acquisition of the planning magnetic resonance image, wherein the second kind of radiation is radio frequency radiation, wherein the working magnetic resonance imaging antenna is used to acquire the planning magnetic resonance image prior to the radiation treatment and to affect patient positioning and/or orientation during the magnetic resonance imaging, where the working magnetic resonance imaging antenna comprises an inner surface to be positioned towards a patient in a way such that it affects or facilitates a position and/or orientation of the patient during the magnetic resonance imaging, wherein the mock-up antenna is used during the radiation treatment delivery to facilitate or affect patient positioning and/or orientation, where the mock-up antenna is substantially transparent to the first kind of radiation and comprises an inner surface to be positioned towards the patient in a way such that it affects or facilitates a position and/or orientation of the patient during the radiation treatment delivery reproducing the patient positioning and/or orientation during the magnetic resonance imaging.

2. The method of claim 1, wherein the inner surface of the mock-up antenna has a shape which is sufficiently similar to a shape of the working magnetic resonance imaging antenna used during the acquisition of the planning magnetic resonance image in order to facilitate or affect the position and/or orientation of the patient during radiation treatment delivery which reproduces the position and/or orientation of the patient during the acquisition of the planning magnetic resonance image.

3. The method of claim 1, wherein the mock-up antenna comprises a connector, wherein the connector is configured to allow a connection between the mock-up antenna and a fixation device, wherein the fixation device is configured to fixate a position of the mock-up antenna during the radiation treatment.

4. The method of claim 1, including positioning the inner surface of the mock-up antenna directly in contact with the patient during the radiation treatment and positioning the inner surface of the working antenna directly in contact with the patient during the acquisition of the planning magnetic resonance image.

5. The method of claim 1, including positioning a thermoweldable material between the inner surface of the mock-up antenna and the patient during the radiation treatment.

6. A mock-up antenna for a kit comprising a working magnetic resonance imaging antenna, wherein the working magnetic resonance imaging antenna is configured to be used for magnetic resonance imaging, and wherein the mock-up antenna is configured to be used during radiation treatment delivery, wherein the radiation treatment is delivered based on a radiation treatment plan, wherein the radiation treatment plan is at least partly based on a planning magnetic resonance image, wherein the planning magnetic resonance image is acquired prior to the radiation treatment, where a first kind of radiation is used during the radiation treatment, wherein a second kind of radiation is used during acquisition of the planning magnetic resonance image, wherein the second kind of radiation is radio frequency radiation, wherein the working magnetic resonance imaging antenna comprises an inner surface configured to be positioned towards a patient in a way such that it affects a position and/or orientation of the patient during the magnetic resonance imaging, wherein the mock-up antenna is substantially transparent to the first radiation and comprises an inner surface configured to be positioned towards the patient in a way such that it affects a position and/or orientation of the patient during the radiation treatment delivery reproducing the patient positioning and/or orientation during the prior magnetic resonance imaging.

7. The mock-up antenna of claim 6, wherein the mock-up antenna comprises a connector, wherein the connector is configured to allow a connection between the mock-up antenna and a fixation device, wherein the fixation device is configured to fixate a position of the mock-up antenna during the radiation treatment.

8. The mock-up antenna of claim 7, further comprising the fixation device, wherein the fixation device is connectable to the connector and is configured to position the mock-up antenna in a position relative to the patient during the radiation treatment delivery which reproduces a position of the working antenna used during the acquisition of the planning magnetic resonance image.

9. The mock-up antenna of claim 6, wherein a shape of the inner surface of the mock-up antenna is sufficiently similar to a shape of the inner surface of the working antenna used during the acquisition of the planning magnetic resonance image such that the position and/or orientation of the patient during the radiation treatment delivery reproduces the position and/or orientation of the patient during the acquisition of the planning magnetic resonance image.

10. The mock-up antenna of claim 6, wherein the inner surface of the mock-up antenna is configured to be directly in contact with the patient during the radiation treatment, and wherein the inner surface of the working antenna is configured to be directly in contact with the patient during the acquisition of the planning magnetic resonance image.

11. A kit comprising a working magnetic resonance imaging antenna configured to be used for magnetic resonance imaging and a mock-up antenna configured to be used during radiation treatment delivery, wherein the radiation treatment is delivered based on a radiation treatment plan, wherein the radiation treatment plan is at least partly based on a planning magnetic resonance image, wherein the planning magnetic resonance image is acquired prior to the radiation treatment, where a first kind of radiation is used during the radiation treatment, wherein a second kind of radiation is used during acquisition of the planning magnetic resonance image, wherein the second kind of radiation is radio frequency radiation, wherein the working magnetic resonance imaging antenna comprises an inner surface configured to be positioned towards a patient in a way such that it affects a position and/or orientation of the patient during the magnetic resonance imaging, wherein the mock-up antenna is substantially transparent to the first radiation and comprises an inner surface configured to be positioned towards the patient in a way such that it affects a position and/or orientation of the patient during the radiation treatment delivery reproducing the patient positioning and/or orientation during the magnetic resonance imaging.

12. The kit of claim 11, wherein a fixation device is connectable to the working antenna and configured to enable positioning of the mock-up antenna during the radiation treatment in a position which reproduces a position of the working magnetic resonance imaging antenna during the acquisition of the planning magnetic resonance image.

13. The kit of claim 11, wherein a shape of the inner surface of the mock-up antenna is sufficiently similar to a shape of the inner surface of the working magnetic resonance imaging antenna such that the position and/or orientation of the patient during the radiation treatment delivery reproduces the position and/or orientation of the patient during the acquisition of the planning magnetic resonance image.

14. The kit of claim 11, wherein the mock-up antenna comprises a connector, wherein the connector is configured to allow a connection between the mock-up antenna and a fixation device, wherein the fixation device is configured to fixate a position of the mock-up antenna during the radiation treatment.

15. The kit of claim 14, further comprising the fixation device connectable to the connector and configured to position the mock-up antenna during the radiation treatment in a position relative to the patient during the radiation treatment delivery which reproduces a position of the working antenna used during the acquisition of the planning magnetic resonance image.

16. The kit of claim 11, wherein the inner surface of the mock-up antenna is configured to be directly in contact with the patient during the radiation treatment, and wherein the inner surface of the working antenna is configured to be directly in contact with the patient during the acquisition of the planning magnetic resonance image.

17. The kit of claim 11, including a thermoweldable material, wherein the thermoweldable material is configured to be positioned between the inner surface of the mock-up antenna and the patient during the radiation treatment.

* * * * *